(12) United States Patent
Kim

(10) Patent No.: US 6,569,916 B2
(45) Date of Patent: May 27, 2003

(54) HIGH REFRACTIVE INDEX TRIAZINE MONOMER

(75) Inventor: Eun Kyoung Kim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 81 days.

(21) Appl. No.: 09/925,479

(22) Filed: Aug. 10, 2001

(65) Prior Publication Data

US 2002/0158352 A1 Oct. 31, 2002

(30) Foreign Application Priority Data

Feb. 24, 2001 (KR) .......................................... 2001-9494

(51) Int. Cl.$^7$ ................................................. C08F 2/46
(52) U.S. Cl. ...................... 522/167; 522/150; 522/151; 522/173; 428/287; 106/287.3; 106/287.32; 264/494; 264/1.1; 264/1.27; 264/1.32; 264/1.34; 264/1.31
(58) Field of Search ................................. 522/150, 151, 522/167, 173; 428/287; 106/287.3, 287.32; 264/494, 1.1, 1.27, 1.32, 1.34, 1.31

(56) References Cited

U.S. PATENT DOCUMENTS

| | | | | |
|---|---|---|---|---|
| 3,637,337 A | * | 1/1972 | Pilling ........................... 8/510 |
| 4,329,384 A | * | 5/1982 | Vesley et al. ............... 428/41.3 |
| 4,330,590 A | * | 5/1982 | Vesley ........................ 428/336 |
| 4,391,687 A | * | 7/1983 | Vesley ...................... 525/330.5 |
| 5,387,682 A | * | 2/1995 | Bonham et al. ............. 544/194 |
| 5,496,504 A | * | 3/1996 | Bonham et al. ............. 252/600 |
| 5,723,513 A | * | 3/1998 | Bonham et al. ............... 522/63 |

FOREIGN PATENT DOCUMENTS

| | | | | |
|---|---|---|---|---|
| EP | 320450 A | * | 6/1989 | .......... C07D/251/38 |
| JP | 4116130 | | 4/1992 | .............. C22C/1/00 |
| JP | 4161411 | | 6/1992 | .............. G02B/5/04 |
| JP | 5188201 | | 7/1993 | .............. G02B/1/04 |
| JP | 6123855 | | 5/1994 | .............. G02C/7/00 |
| JP | 6167230 | | 6/1994 | ........... F02D/29/02 |
| JP | 6202049 | | 7/1994 | .............. G02C/7/02 |
| JP | 11263811 | | 9/1999 | .............. C08F/26/06 |
| JP | 2001091834 | | 4/2001 | .............. G02B/5/04 |

OTHER PUBLICATIONS

Thurston, J.T. et al., Journal of the American Chemical Society. vol. 73, No. 7; Jul. 6, 1951.

Kim, Jae Jong et al., Kobunshi Ronbunshu. vol. 56, No. 3; pp. 159–165; Mar. 1999.

* cited by examiner

Primary Examiner—James J. Seidleck
Assistant Examiner—Sanza L. McClendon
(74) Attorney, Agent, or Firm—Fitzpatrick, Cella, Harper & Scinto

(57) ABSTRACT

The present invention relates to a triazine type monomer, and more particularly, to a 1,3,5-triazine type monomer characterized by having at least one amine group and at least two sulfur atoms, which can be used in manufacturing transparent optical resins having excellent refractive index, surface hardness and absorbance as well as an improved workability and the ability to control a wide range of refractive index according to the change in composition by the monomer itself at room temperature or by polymerizing the monomer with a comonomer in the presence of an organic solvent or an initiator.

7 Claims, No Drawings

HIGH REFRACTIVE INDEX TRIAZINE MONOMER

FIELD OF THE INVENTION

The present invention relates to a triazine type monomer, and more particularly, to a 1,3,5-triazine type monomer expressed in the following formula (I) characterized by having at least one amine group and at least two sulfur atoms. The triazine monomers can be used in manufacturing transparent optical resin having excellent refractive index, surface hardness and light transparency as well as an improved workability and the ability to control a wide range of refractive index by adjusting composition by the monomer itself at room temperature or by polymerizing the monomer with a comonomer in the presence of an organic solvent or an initiator.

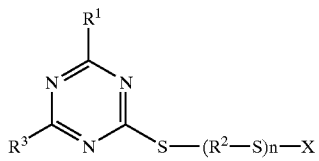

(I)

BACKGROUND OF THE INVENTION

Plastic transparent optical materials have been welcomed as matrices for manufacturing optical lenses, optical filters and transparent panels because they are light-weighted, less fragile and also more easily dyeable as compared to inorganic materials. In particular, the importance of developing plastics having high surface hardness and high refractive index has been much emphasized lately since the massive introduction of diethylene glycol biscarbonate allyl(CR-39) compounds in production of optical lens. However, CR-39 has a relatively low refractive index of below 1.50 even after curing process and thus the central region of the lens to be manufactured has to be thick in case of a convex lens while the periphery has to be thick in a concave lens thus resulting in production of heavy lenses.

Many lines of studies to develop monomers with high refractive index have been initiated since 1986. Various types of monomers including an alkyl- and meta-alkyl group were developed in 1990s, thus improving the refractive index of lenses to some extent. Nevertheless, the refractive index of those monomers were $n_D^{20}$: 1.526–1.519 and the refractive index of the resulting lenses produced accordingly was approximately $n_D^{25}$: 1.549. Therefore, the development of monomers having refractive index of higher than 1.55 still remains as a long-felt need.

Monomers having high refractive index can shorten the focal distance of given lenses and thus produce thin lenses; hence, they can be widely used in manufacturing optical lenses, transparent panels, optical heads and other light-weighted optical products. Polycarbonates, being a transparent optical resin, have rather high refractive index of 1.59, however, they have a few drawbacks that they are deficient in optical homogeneity and have poor anti-solvent and abrasion resistance properties thus not being suitable for manufacturing optical products requiring high transparency and high surface hardness.

To resolve the above problems, compounds with high refractive index containing an aromatic ring, thiol or a halogen group in the molecule have been developed. Recently, polyurethanes were developed to increase both the refractive index and the Abbe number. However, these polyurethanes are also not recommended because they would impede hard coating and multi-coating and also result in relatively low lens production yield due to their poor thermal stability and low surface hardness.

Japanese Patent Publication 11-263811 discloses a method of preparing a curing composition with good workability to give a cured product, consisting of a cyanuric acid or an isocyanuric acid, with excellent optical properties and impact resistance. However, the cured product has refractive index of about 1.575, which is lower than the refractive index of lenses manufactured using polyurethanes. Therefore the development of monomers with excellent thermal stability, surface hardness and high refractive index as well as processability with other monomers is still highly required.

SUMMARY OF THE INVENTION

The inventors of the present invention developed a method to prepare a triazine-containing monomer as expressed in the formula (I) with refractive index higher than 1.6 and the optical products manufactured from the monomer were shown to have excellent physical properties with respect to transparency, refractive index, surface hardness and thermal stability. Therefore, the object of this invention is to provide a monomer and a composition containing this monomer which can be effectively used in optical industry such as manufacturing functional optical lenses, optical filters, optical displayers, optical discs or optical heads and other optical devices.

DETAILED DESCRIPTION OF THE INVENTION

The present invention relates to a triazine type monomer, and more particularly, to a 1,3,5-triazine type monomer expressed in the following formula I characterized by having at least one amine group and at least two sulfur atoms

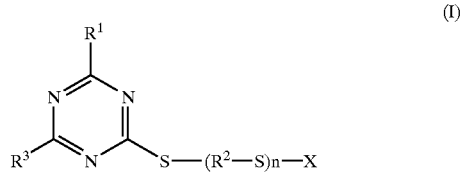

(I)

wherein $R^1$ is a secondary or a tertiary amine group selected from the group consisting of $R^4NH-$, $R^4R^5N-$ or

$R^4$ and $R^5$ are independently $C_1$–$C_{22}$ alkyl or cycloalkyl; $R^6$ is a $C_1$–$C_{15}$ alkylene or aromatic ring forming alkenes such as $-CH=CH-CH=CH-$ or $-CH=CH-CH_2-CH=CH-$; $R^2$ is $C_1$–$C_{22}$ linear alkylene, branched alkylene, or a 1,3-,1,4-benzene ring; $R^3$ is $R^1$ or $-S-(R^2-S)_n-X$; X is an acryl-, methacryl or $C_2$–$C_{10}$ alkene group; and n is an integer of 1–10.

The method of preparing the above triazine type monomer used in the present comprises the following steps of:

(a) preparing triazine expressed in the following formula (IV) by reacting 2,4,6-trichloro-1,3,5-triazine with secondary- or tertiary amine;

(b) preparing triazine expressed in the following formula (V) by reacting said triazine obtained in the above step (a) with NaSH;
(c) preparing triazine expressed in the following formula (VI) by reacting said triazine obtained in the above step (b) with a thiol derivative expressed as Y—($R^2$—S)$_n$—H in the presence of a mixed catalyst; and
(d) preparing triazine expressed in the above formula (I) by reacting said triazine obtained in the above step (c) with;
  (i) a compound selected from a group consisting of acryloyl chloride, methacryloyl chloride, and allyl bromide in the presence of a mixed catalyst; or
  (ii) propionyl chloride and then treat with a base,

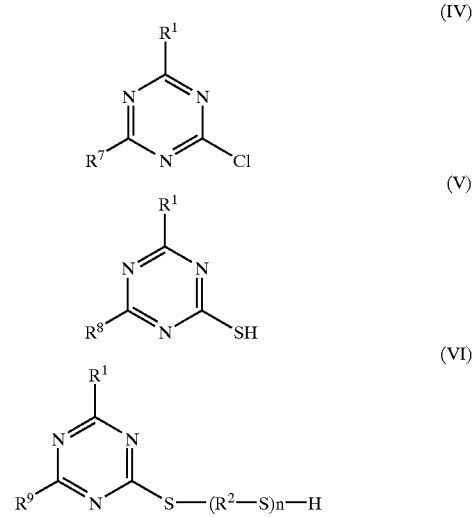

(IV)

(V)

(VI)

wherein $R^1$ is a secondary or a tertiary amine group selected from the group consisting of $R^4$NH—, $R^4R^5$N— or

$R^4$ and $R^5$ are independents $C_1$–$C_{22}$ alkyl or cycloalkyl; $R^6$ is $C_1$–$C_{15}$ alkylene or an aromatic ring forming alkenes such as —CH=CH—CH=CH— or —CH=CH—CH$_2$—CH=CH—; $R^7$ is the same as $R^1$ or Cl; $R^8$ is the same as $R^1$ or SH; $R^9$ is the same as $R^1$ or S—($R^2$—S)$_n$—H; $R^2$ is $C_1$–$C_{22}$ linear alkylene, branched alkylene, or a 1,3-,1,4-benzene ring; $R^3$ is $R^1$ or —S—($R^2$—S)$_n$—X; X is an acryl-, methacryl or $C_2$–$C_{10}$ alkene group; n is an integer of 1–10; and Y is a leaving group selected from Cl, Br and OH. Thus obtained triazine monomers of the present invention can be used to manufacture transparent optical products via self-polymerization of these monomers or copolymerization in the presence of comonomer(s). The overall physical properties of the optical products such as refractive index can be adjusted by preparing the polymerizable resin composition so that it comprises 1–98 wt % of the monomer of the present invention; 1–98 wt % of either an aromatic radical polymerizable monomer or a comonomer with an unsaturated group; and 0.5–5 wt % of an initiator.

The methods of manufacturing of plastic products using the above composition can include various procedural methods such as thermosetting of the resin composition at 10–130° C., radiation curing of the resin composition at 10–130° C., or first radiation curing the resin composition at 10–130° C. followed by thermo setting of the resin composition at 10–130° C.

The present invention is explained in greater detail by means of the methods of manufacturing a triazine type monomer with high refractive index.

The novel triazine type monomers are manufactured by the reactions shown below, wherein polymerizable triazine type monomers with high refractive index expressed in the formula I are manufactured by the method comprising steps of substitution of at least one chloride groups in 1,3,5-triazine-chloride with an amine group, substitution of at least one of the remaining chloride groups in the 1,3,5-triazine-chloride with a thiol group and reacting with a thiol derivative, and introduction of an unsaturated group.

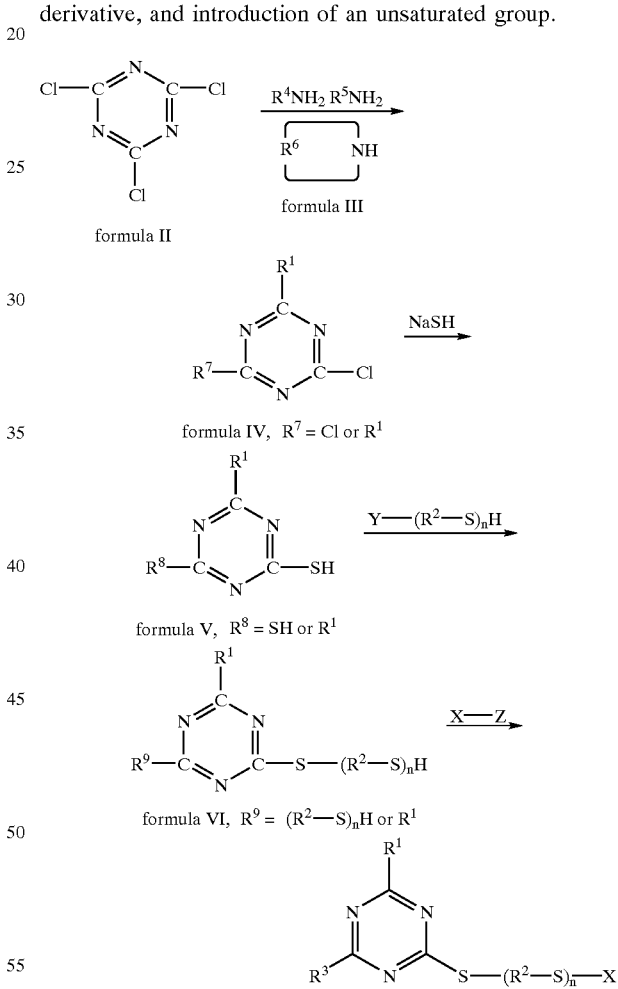

In the above reactions, Y and Z represent a leaving group such as Cl, Br or OH, respectively.

1) Step 1: Reacting 2,4,6-trichloro-1,3,5-triazine with a Secondary or a Tertiary Amine Chloro-1,3,5-triazine [formula (IV)] having at least one amine group is produced by reacting 2,4,6-trichloro-1,3,5-triazine[formula (II)] with amine[formula (III)] according to the method by Thurston et al. (J. T. Thurston, J. R. Dudley, D. W. Kaiser, I. Hechenbleikner, F. C. Scaefer, D. Holm-Hansen, *J. Am. Chem. Soc.,* 1951, 73, 2981).

2) Step 2: Reacting with NaSH

Triazinethiol wherein a chloride is substituted with a thiol[formula (V)] is produced by reacting the Chloro-1,3,5-triazine [formula (IV)] having at least one amine group obtained in the above step 1 with NaSH according to the method by Kobunshi Ronbunshu [Kobunshi Ronbunshu (1999), 56(3), 159–165, Kim, Jae Jong; Oishi, Yoshiyuki; Hirahara, Hidetoshi; Mori, Kunio].

3) Step 3: Reacting with Y—$(R^2$—$S)_n$—H in the Presence of a Mixed Catalyst

A compound represented by the formula VI is produced when the formula V is reacted with Y—$(R^2$—$S)_n$—H. The solvent that can be used here is one or a mixture of more than two selected from the group consisting of toluene, benzene, dichloromethane and chloroform. The catalyst used here is one or a mixture of more than two selected from the group consisting of such as NaOH, KOH, tetrabutyl ammoniumchloride and benzenetriethyl ammoniumchloride (BTEAC) of quarternary ammonium salts. Reaction is performed at 30–120° C., preferably 50–80° C., and for 2–48 hrs, preferably for 4–16 hr.

4) Step 4: Reacting with a Compound Selected From the Group Consisting of Acryloyl Chloride, Methacryloyl Chloride and Allyl Bromide, or with Propionyl Chloride in the Presence of a Mixed Catalyst Followed by Base Treatment There are two methods to produce the compound represented by the formula (I) by using the compound represented by the formula (VI).

The first method is to react the compound represented by the formula (VI) with a compound selected from the group consisting of acryloyl chloride, methacryloyl chloride and allyl bromide. The solvent used in the reaction is one or a mixture of more than two selected from the group consisting of toluene, benzene, dichloromethane and chloroform. The catalyst used here is one or a mixture of more than two of phase transfer catalyst selected from the group consisting of such as NaOH, KOH, tetrabutyl ammoniumchloride and benzenetriethyl ammoniumchloride (BTEAC) of quarternary ammonium salts. Reaction is performed at −10 to 80° C., preferably 0–60° C. Reaction is performed for 0.5–48 hr, preferably for 1–16 hr.

The second method is to react the compound represented by the formula (VI) with propionyl chloride followed by treatment with a base. The solvent used in the reaction is one or a mixture of more than two selected from the general organic solvent including dioxane, tetrahydrofuran and acetone. Reaction is initiated by adding propionyl chloride dropwise into the reactant containing the compound represented by the formula (VI) at −5 to 50° C., preferably 0–25° C., and stirring the mixture for 10 min–5 hr, preferably 0.5–3 hr. To this reactant is added general amine such as triethylamine and is allowed to react at −5 to 50° C., preferably 0–25° C., for 1–48 hr, preferably 5 min to 16 hr and finally transparent polymerizable monomer having refractive index of more than 1.6 is obtained.

The reaction of manufacturing the compound represented by the a formula (I) from the compound represented by the formula (V) can be proceeded continuously without necessitating a purification step. The above reaction, however, can be reinitiated after separation and purification of compounds obtained in each step, if higher purity is required. Thus obtained monomers of the present invention are recommended as optical materials for manufacturing optical products such as camera lenses and plastic lenses for glasses, which require excellent surface hardness, transparent, odorless and light-weighted properties.

Below are the preferred embodiments of each component of the resin composition according to the present invention.

The polymerizable resin composition of the present invention comprises 1–98 wt % of a monomer expressed in the formula (I); 1–98 wt % of either an aromatic radical polymerizable monomer or a comonomer with an unsaturated group; and 0.5–5 wt % of an initiator, and overall physical properties (e.g., refractive index) can be modified by adjusting the amount of the above-mentioned components within the range mentioned above.

1) Novel Triazine Type Monomer

The compound represented by the formula (1), which is included as a polymerizable monomer, has relatively high refractive index and enables to perform a radical polymerization by means of UV light or heat and thus becoming very useful in manufacturing transparent optical compositions with high refractive index.

The examples of preferred chemical structures of the formula (I) are as follows.

Structure 1

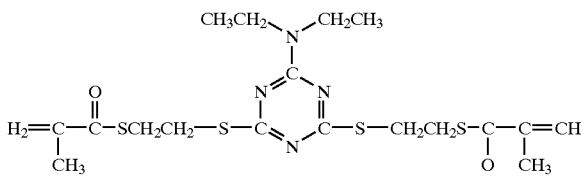

Structure 2

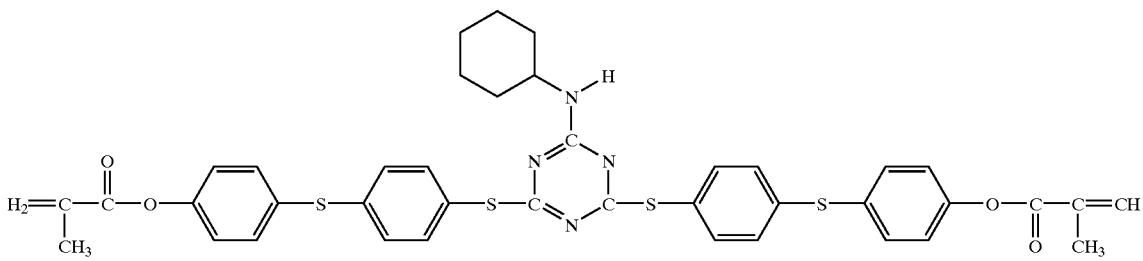

-continued
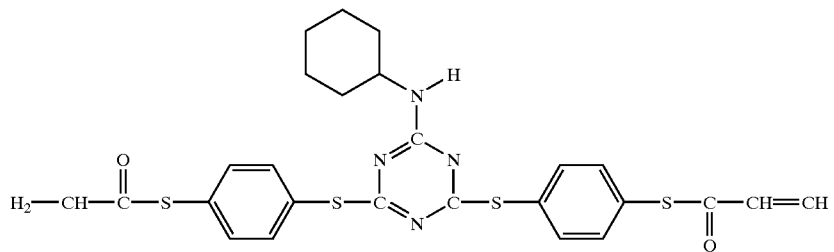
Structure 3
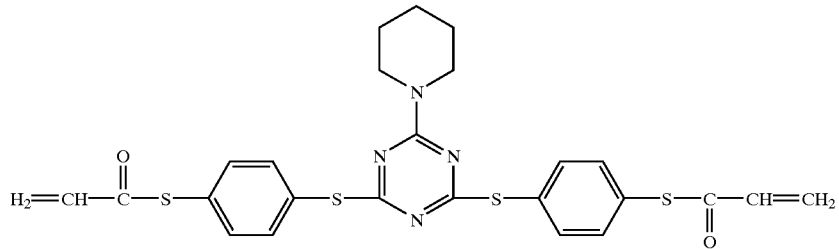
Structure 4
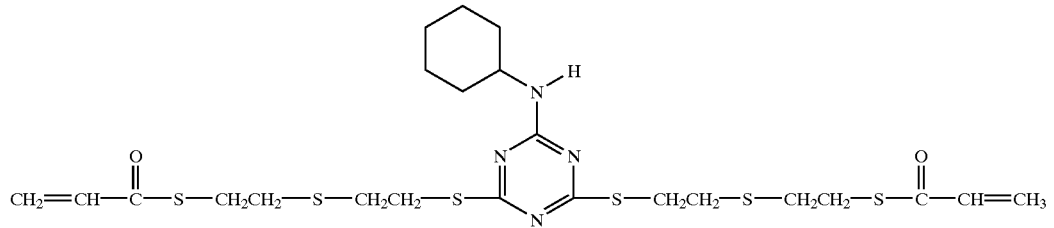
Structure 5
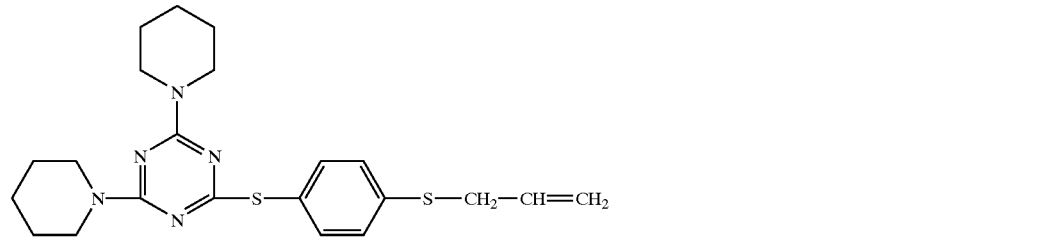
Structure 6
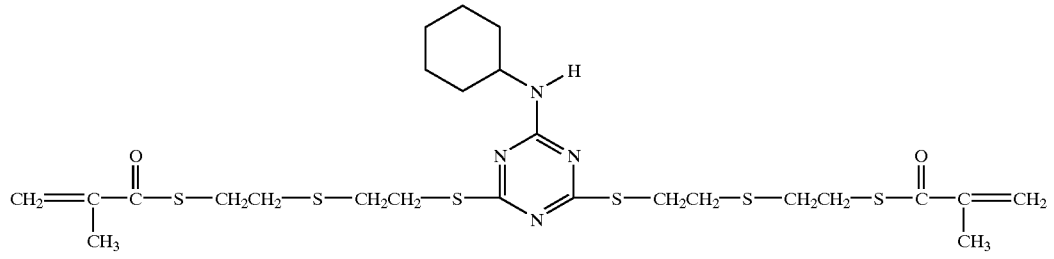
Structure 7
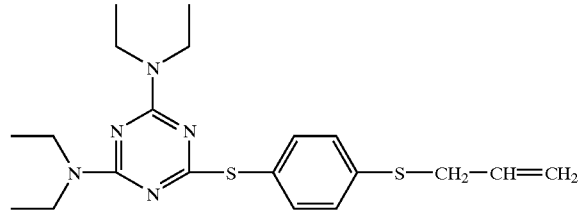
Structure 8

-continued

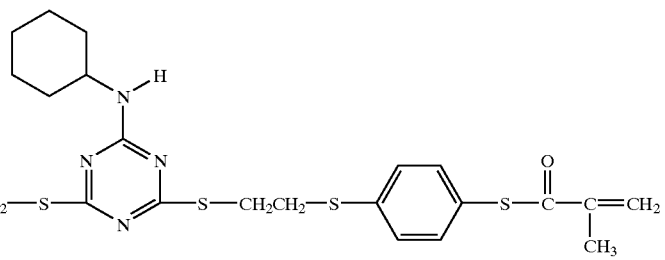
Structure 9

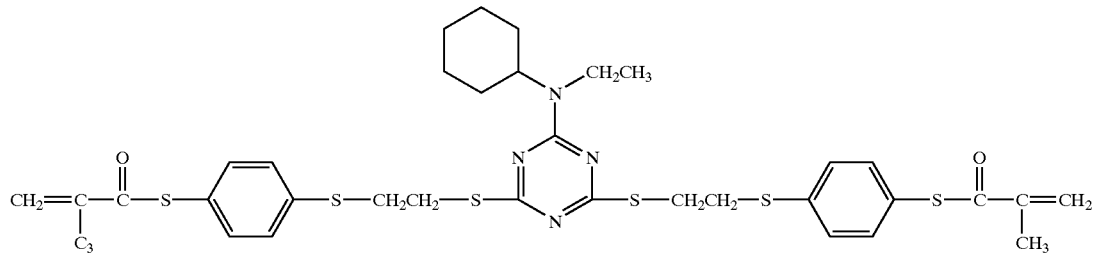
Structure 10

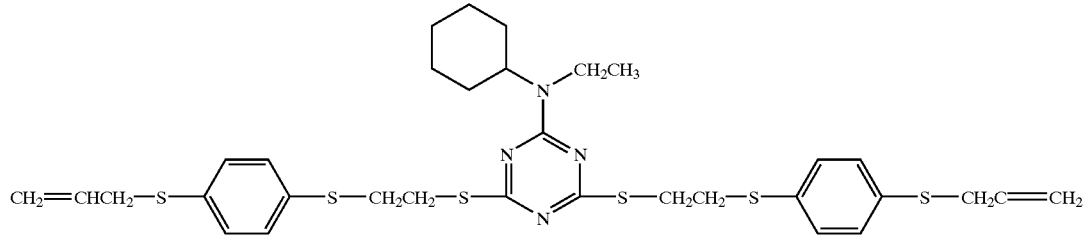
Structure 11

2) An Aromatic Radical Polymerizable Monomer or a Comonomer with an Unsaturated Group The examples of the aromatic radical polymerizable monomers which can be used along with the compound represented by the formula (I) are:

Diethylene glycol dimethacrylate, triethylene glycol dimethacrylate, tetraethylene glycol dimethacrylate, butanediol dimethacrylate, hexamethylene dimethacrylate, bisohenol A dimethacrylate, 2,2-bis(4-methacryloyloxyethoxy-3,5-dibromophenyl)propane, 2,2-bis(4-methacryloyloxyethoxyphenyl)propane, 2,2-bis(4-methacryloyloxydiethoxyphenyl)propane, 2,2-bis(4-methacryloyloxytriethoxyphenyl)propane, 2,2-bis(4-methacryloyloxypentaethoxyphenyl)propane, bis-4-vinylbenzyl ether, bis-4-vinylbenzyl sulfide, 1,2-(p-vinylbenzyloxy)ethane, 1,2-(p-vinylbenzylthio)ethane, bis-(p-vinylbenzyloxyethyl)sulfide.

Other usable radical polymerizable monomers are disclosed in Japanese Patent Publication Nos. 4-11613, 4-161411, 5-188201, 6-123855, 6-202049, 6-16723, and below are the selected examples of their structures.

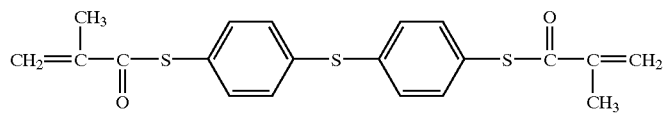
Structure 12

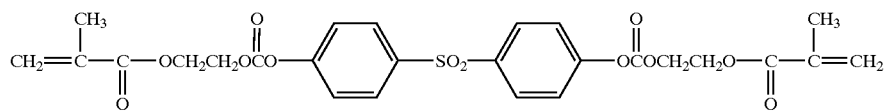
Structure 13

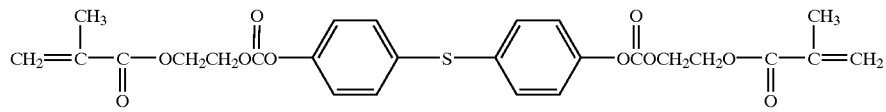
Structure 14

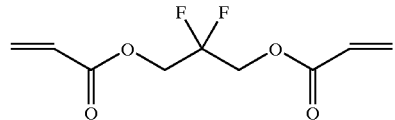
Structure 15

Structure 16

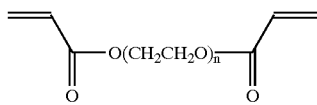

Structure 17

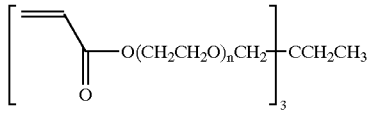

Structure 18

In addition to the monomers shown in the above, one or more comonomers such as NK55[a mixed composition of aromatic dimethacrylate, α-methylstyrene, tetra(ethylene glycol) dimethacrylate, isopropenyl benzene, and tribromophenyl acrylate], CR39(bisallylethylene glycol carbonate) (Aldrich Chemical Co., Ltd., USA), α-methylstyrene, styrene, polyethyleneoxymethacrylate, polyethyleneoxyacrylate, polyethyleneoxydiacrylate, polyethyleneoxytriacrylate, and other comonomers with an unsaturated group can be added for the copolymerization with formula (I).

3) Initiators

Initiators, after decomposition into a radical by either heat or UV irradiation, can initiate polymerization of triazine monomers and can be selected one or more from the group consisting of 2,2'-azobisisobutyronitrile (AIBN), benzoyl peroxide (BPO), diisopropyl peroxydicarbonate (IPP), tertiary butyl hydroperoxide (TBPO), t-butyl peroxy 2-ethylhexanoate and other thermo-setting initiators; or one or mixture of initiators selected from the group consisting of Irgacure (1-hydrocyclohexyl phenylketone, benzophenone, 2-hydroxy-1-[4-(hydroxyethoxy)phenyl]-2-methypropanone, 2,2-dimethoxy-2-phenylacetophenone, fluorinated diaryltitanocene (product of Ciba-Geigy Co., Ltd., Switzerland) and known photo initiators such as 2,2-bis (hydroxymethyl)propionic acid (DPMA).

Further, aliphatic unsaturated compounds and organic solvents can be added in addition to the above-mentioned active components for the purpose of adjusting film thickness as well as viscosity. Additives that delay the polymerization, polymerization catalysts, UV absorbents and anti-coloring agents for enhancing abrasion resistance property can be also used, and stirring, filtration and defoaming processes can be also introduced during manufacturing of compositions.

The resins manufactured using the resin composition according to the present invention by means of photo polymerization or thermal polymerization are characterized by having excellent transparency, surface hardness, abrasion resistance and refractive index. Therefore, the resin composition of the present invention can be used in manufacturing transparent optical products such as functional optical lenses, filters, imaging, display elements or optical integrated elements, holograms, optical discs, optical recording materials, optical pickup parts and the like.

The resin composition of the present invention can be coated on glass plates, ITO, silicon wafer and other support membranes. The resin composition can be molded by radiation curing or thermosetting by putting it into molds made of various materials and it is recommended to introduce the resin composition into molds or gaskets by the pressure of air or nitrogen gas. Thermosetting is usually proceeded for 3–48 hr depending the amount of resin composition and the initiator. When using benzoylperoxide (BPO) as initiators, for example, the thermosetting is performed at −20–120° C. and it is preferred to cure for 30 sec −2 hr using UV lamp, UV curing equipment and a Zenon lamp. In case of photo polymerization of a composition comprising 88 g of a monomer represented by the formula (I), 8 g of a compound represented by the Structure 13, 2 g of Irgacure 184 photo initiator and 8 g of tetrahydrofuran solvent, a film with 3 μm of thickness, 1.65 of refractive index and 3H of pencil hardness is formed when cured by UV curing equipment for 5 min at room temperature.

The resin composition of the present invention can be used in manufacturing transparent optical products such as plastic lenses, films, light transparent films and image forming materials.

First, plastic lenses can be manufactured by inserting resin composition into a mold followed by thermal curing. Here, the temperatures are changed stepwise during the heat curing process as follows: the temperature is kept at between room temperature and 70° C. for 30–360 min for the initiation of decomposition of an initiator and prepolymerization, 70–80° C. for 110–180 min, 85–95° C. for 110–130 min, 110–130° C. for 30–240 min and is then allowed to be naturally cooled down.

Films can be manufactured by inserting resin composition into a glass mold followed by photo curing by UV irradiation for 30 sec to 2 hr. Also, the light transparent films can be manufactured by coating on a plate such as silicon wafer followed by UV irradiation for 30 sec to 2 hr. The radiant curing of these light transparent films and thin films can be performed by using a UV lamp, a UV curing equipment or a Zenon lamp.

Images are to record mask images on a plate, wherein resin composition is coated on a silicon wafer, a transparent plastic plate, an ITO or a glass plate and then the images are recorded by UV irradiation. Then, the mask is removed, dipped into a solvent and then dried to reveal the embossing of the mask images (recorded part). The embossing part of the masking images can be stable for more than a year. The examples of the above plates include silicon wafers, transparent plates, ITO and glass.

Hereunder is given a detailed description of the present invention using the following examples, however, it should not be construed as limiting the scope of the present invention.

The following Preparation Examples 1 and 2 show only a part of the methods to synthesize the starting materials used to prepare starting materials of the present invention and other starting materials can be easily prepared by using the known methods or by purchasing the commercial products.

PREPARATION EXAMPLE 1

Synthesis of 6-diethylamino-2,4-dichloro-1,3,5-triazine 52.99 g of NaHCO$_3$ was added into a reactor and dissolved in 300 mL of distilled water while cooling down the reactor into 0–2° C. and then 51.7 mL of diethylamine [(C$_2$H$_5$)$_2$NH] was added to the reactor. A solution of 2,4,6-trichloro-1,3,5-triazine (92.2 g) in 300 mL of dioxane in a dropping funnel kept at 0–5° C. was slowly added into the above reactor and was allowed to react for 2 hr at 0–5° C. to give 6-diethylamino-2,4-trichloro-1,3,5-triazine white precipitate. The white precipitate was then filtered and recrystallized from benzene to afford pure 6-diethylamino-2,4-trichloro-1,3,5-triazine (yield 90%).

IR (KBr, cm$^{-1}$): 2968–2870(CH$_3$, CH$_2$), 1556(C=N)

$^1$H-NMR (DMSO-d$_6$): 1.12(t, 6H, CH$_3$), 3.59(q, 4H, CH$_2$)

PREPARATION EXAMPLE 2

Synthesis of 6-cyclohexylamino-2,4-dichloro-1,3,5-triazine 2,4,6-Trichloro-1,3,5-triazine (92.2 g) was dissolved in 300 mL of dioxane at room temperature. 53 g of Na$_2$CO$_3$ was dissolved in 300 mL of distilled water and was slowly added into the above solution. Cyclohexylamine (49.95 g) in a dropping funnel was slowly added into the above solution while stirring at 0–5° C. for 2 hr. The stirring was continued for another 3 hr at 0° C., 1 hr at room temperature, and the resultant white precipitate was then filtered and washed with water. The white precipitate was dissolved in methylenechloride (MC) and washed with water and MC was evaporated. Finally, 6-cyclohexylamino-2,4-dichloro-1,3,5-triazine having a substituted cyclohexyl was obtained after drying and solvent removal. The yield was more than 90%.

$^1$H-NMR (DMSO-d$_6$): 1.10–1.45(m, 6H, CH$_2$), 1.82–1.95 (m, 4H, CH$_2$), 3.56(m, 1H, CH), 5.17(s, 1H, NH)

PREPARATION EXAMPLE 3

Synthesis of 6-piperidyl-2,4-dichloro-1,3,5-triazine

In the above preparation example 2, cyclohexylamine was replaced with 51 g of piperidine and obtained triazine derivative having a substituted piperidyl group. The yield was 80%.

$^1$H-NMR (DMSO-d$_6$): 1.54–1.58(m, 6H, CH$_2$), 3.64–3.70 (m, 4H, CH$_2$)

PREPARATION EXAMPLE 4

Synthesis of 6-diethylamino--2,4-dithiol-1,3,5-triazine

The compound (44.2 g) prepared in the above preparation example 1 was added into a reactor along with 200 mL of DMF. NaSH.2H$_2$O (55.25 g) was dissolved in a mixture consisting of 150 mL of DMF and 150 mL of distilled water and then added into a separatory funnel. It was added dropwise into the reactor while keeping the temperature of a reactor below 50° C., and after the adding was completed the reaction was continued further for 6 hr while keeping the temperature at 60° C. 160 mL of 10% HCl solution was slowly added into the reactor to adjust the pH into 2–3 to generate white precipitate. The white precipitate was filtered, washed with distilled water several times, dried in a 100° C. oven for 24 hr, dried in an 80° C. vacuum oven for 24 hr and 6-diethylamino--2,4-dithiol-1,3,5-triazine was finally obtained. The yield was 90%.

IR (KBr, cm$^{-1}$): 2968–2870(CH$_3$, CH$_2$), 1602, 1539, 1502(C=N);

$^1$H-NMR (DMSO-d$_6$): 0.90–0.94(t, CH$_3$), 3.35–3.42(q, CH$_2$)

PREPARATION EXAMPLE 5

Synthesis of 6-cyclohexylamino-2,4-dithiol-1,3,5-triazine

The compound (49.4 g) prepared in the above preparation example 2 was dissolved in 200 mL of DMF. NaSH.2H$_2$O (55.25 g) was dissolved in a mixture consisting of 150 mL of DMF and 150 mL of distilled water and then added into an aliquot funnel. It was slowly added into a reactor for 40 min at 31° C. After the addition was completed, the temperature was raised to 70° C. and the reaction was continued further for 5 hr and then cooled down to a room temperature. 350 mL of 10% HCl solution was slowly added into the reactor to adjust the pH into 2–3 to generate white precipitate. The white precipitate was filtered, washed with distilled water several times, dried and 6-cyclohexylamino-2,4-dithiol-1,3,5-triazine was finally obtained. The yield was 93%.

Purification: The above product was dissolved in a mixture solution consisting of 500 mL of 10% NaOH and 500 mL of methanol and the insoluble substances were filtered out. 10% HCl solution was slowly added to adjust the pH into 2–3 and to generate white precipitate. The white precipitate was washed with water a few times and dried. The yield was 90%.

$^1$H-NMR (DMSO-d6): 1.10–1.38(m, 6H, CH$_2$), 1.82–1.95(m, 4H, CH$_2$), 3.56(m, 1H, CH), 3.99(s, 1H, NH), 12.82(s, 2H, SH)

PREPARATION EXAMPLE 6

Synthesis of 6-piperidyl-2,4-dithiol-1,3,5-triazine

The compound (50 g) prepared in the above preparation example 3 was allowed to react as in the preparation example 5. The product was purified and 6-piperidyl-2,4-dithiol-1,3,5-triazine was finally obtained. The yield was 90%.

$^1$H-NMR (DMSO-d6): 1.48–1.62(m, 6H, CH$_2$), 3.59–3.72(m, 6H, CH$_2$), 12.85(s, 2H, SH)

PREPARATION EXAMPLE 7

Synthesis of the Compound Structured as 18

2-Mercaptoethylsulfide (19.6 mL) was added into a 500 mL 3-neck reactor made of pressure-resistant glass and then 29.6 mL of 3-chloropropionyl chloride was added dropwise at room temperature using an aliquot funnel into the reactor. The mixture was allowed to react for 5 hr while keeping the temperature at 40–50° C. Then, 150 mL of toluene and 100 mL of 10% NaOH solution were added into the above reactor and the whole mixture was stirred for 2 hr at room temperature. After the organic phase was removed, the remainder was added again into the reactor along with 44.6 mL of triethylamine and they were allowed to react for 8 hr at room temperature. 200 mL of distilled water was added to the reactor to wash the product and toluene was removed under a reduced pressure. Finally, a monomer represented by the formula (XVIII) having refractive index $_nD19.9$: 1.5800, and viscosity cp: 2.88/2.95° C. was obtained. The yield was 98%.

$^1$H-NMR (DMSO-d$_6$): 2.67(m, 4H, CH$_2$), 2.88(m, 4H, CH$_2$), 6.47(m, 4H, CH$_2$), 6.64(m, 2H, CH)

EXAMPLE 1

Synthesis of 6cyclohexylamino-2,4-di(4-thiol-phenyl)thiol-1,3,5-triazine

KOH (42.1 g) was added into a reactor and dissolved by adding 200 mL of water. Then, 24.2 g of the compound prepared in the preparation example 5 was added to the reactor while stirring and was also added with 100 mL of benzene and 1.59 g of benzyltriethylammonium chloride (BTEAC). 4-Bromobenzenethiol (39.7 g) dissolved in 200 mL of benzene was added dropwise into the reactor using an aliquot funnel while keeping the reaction temperature below 60° C. After setting the temperature of the reactor at 60–70° C., the reactants were stirred further for 10 hr and then dissolved by adding 400 mL of 10% NaOH solution and insoluble substances were removed. 10% HCl solution was slowly added into the reactor to adjust the pH into 2–3 to generate white precipitate. The white precipitate was filtered, washed with distilled water several times, dried to obtain 6-cyclohexylamino-2,4-di(4-thiol-phenyl)-1,3,5-triazine was finally obtained. The yield was 80%.

$^1$H-NMR (DMSO-d$_6$): 1.09–1.40(m, 6H, CH$_2$), 1.83–1.94 (m, 4H, CH$_2$), 3.27(s, 2H, SH), 3.56(m, 1H, CH), 7.03–7.14 (m, 8H, aromatic), 14(s, 1H, NH)

EXAMPLE 2

Synthesis of 6-cyclohexylamino-2,4-di(4-acrylthio-phenyl)thio-1,3,5-triazine KOH (6.17 g g) was dissolved in 50 mL of water and then added with 22.93 g of the compound prepared in the above example 1. Then, 100 mL of acetone and 10 mL of 3-chloropropionyl chloride were added dropwise using a separatory funnel. Stirring was continued for 1 hr at room temperature and 15.3 mL of triethylamine was added into the reactor dropwise for 40 min at 18° C. The reaction was continued further for 10 hr while keeping the temperature of the reactor at 10–20° C. Product, 6-cyclohexylamino-2,4-di (4-acrylthio-phenyl)thio-1,3,5-triazine having refractive index of 1.65 was obtained by extracting with MC and water, washing the organic layer with 10% HCl, and then neutralizing with NaOH solution, extracting with MC, purifying, and final drying. The yield was 90%. $^1$H-NMR (DMSO-d$_6$): 1.12–1.40(m, 6H, CH$_2$), 1.78–1.94(m, 4H, CH$_2$), 3.56(s, 1H, CH), 6.60(m, 2H, CH$_2$), 6.79(m, 2H, CH$_2$), 6.96(m, 2H, CH), 7.20(m, 4H, aromatic), 7.46(m, 4H, aromatic), 14(s, 1H, SH)

EXAMPLE 3

Synthesis of 6-cyclohexylamino-2,4-di(4-methacrylthio-phenyl)thio-1,3,5-triazine The compound (7.2 g) prepared in the above Preparation Example 5, 8.4 g of KOH and 1.14 g of BETAC, a phase transfer catalyst, were dissolved in 100 mL of distilled water in a reactor. Then, aqueous solution, wherein 11.53 g of 4-bromobenzenethiol was dissolved in toluene/MC(50 mL/50 mL), was slowly added into the reactor dropwise using a separatory funnel at room temperature. The reaction was performed for 3 hr while maintaining the temperature of the reactor at 60–70° C., cooled down, and was added with a mixture consisting of 6.48 g of methacryloyl chloride and 50 mL of MC dropwise. After 10 hr of reaction at room temperature, 50 mL of 10% NaOH solution and 100 mL of MC were added, thoroughly stirred and then the organic phase was separated and washed with distilled water several times. After MC was evaporated, a monomer having $_nD^{198}$:1.6231 was obtained. The yield was 85%.

$^1$H-NMR (DMSO-d$_6$): 1.12–1.38(m, 6H, CH$_2$), 1.81–1.92 (m, 4H, CH$_2$), 1.98(s, 6H, CH$_3$), 3.55(m, 1H, NH), 6.63(m, 2H, CH$_2$), 6.81(m, 2H, CH$_2$), 7.21(m, 4H, aromatic), 7.43 (m, 4H, aromatic), 14.30(s, 1H, SH)

EXAMPLE 4

Synthesis of 6-diethylamino-2,4-di(4-methacrylthio-phenyl)thio-1,3,5-triazine The compound (8.65 g) prepared in the Preparation Example 1, 15.5 g of 4-bromobenzenethiol, 80 mL of TMS and 0.2 mol/21.2 g of Na$_2$CO$_3$ were added into a reactor and heated to 100–110° C. and allowed to react for 3 hr. Then, it was cooled down to room temperature and was slowly added with 8.88 g of methacryloyl chloride dropwise. Upon completion of adding, the mixture was allowed to react for 10 hr at room temperature, extracted twice with 100 mL of MC, mixed together and washed with distilled water a few times, and MC was evaporated under a reduced pressure to obtain a monomer having $_nD^{443}$:1.5906 was obtained. The yield was 86%.

$^1$H-NMR (DMSO-d$_6$): 1.18(m, 6H, CH$_3$), 1.91(s, 6H, CH$_3$), 3.62(m, 4H, CH$_2$), 6.62(m, 2H, CH$_2$), 6.81(m, 2H, CH$_2$), 7.36(m, 4H, aromatic), 7.45(m, 4H, aromatic)

EXAMPLE 5

Synthesis of 6-diethylamino-2,4-di(4-methacrylthioethanephenyl)thio-1,3,5-triazine The compound (22.1 g) prepared in the Example 1, 19.8 g of 1,2-ethanedithiol, 150 mL of TMS and 0.25 mol/24.5 g of Na$_2$CO$_3$ were added into a reactor and heated to 110–120° C. and allowed to react for 3 hr. Then, it was cooled down to room temperature and was slowly added with 21.87 g of methacryloyl chloride dropwise at 35° C. Upon completion of adding, the mixture was allowed to react for 10 hr at room temperature, extracted twice with 150 mL of MC, mixed together and washed with distilled water several times, and MC was evaporated under a reduced pressure to obtain a polymerizable monomer having $_nD^{20.1}$:1.6321 was obtained. The yield was 76%.

$^1$H-NMR (DMSO-d$_6$): 1.18(m, 6H, CH$_3$), 1.91(s, 6H, CH$_3$), 3.62(m, 4H, CH$_2$), 6.62(m, 2H, CH$_2$), 6.81(m, 2H, CH$_2$), 7.36(m, 4H, aromatic), 7.45(m, 4H, aromatic)

EXAMPLE 6

Synthesis of 6-piperyl-2,4-di(4-methacrylthiophenyl-4'-phenyl)thio-1,3,5-triazine The compound (44.2 g) prepared in the Preparation Example 1, 1.67 g of 4,4'-thiodiphenol, 300 mL of TMS and 47.7 g of Na$_2$CO$_3$ were added into a reactor and heated to 110–120° C. and allowed to react for 3 hr. The mixture was adjusted to pH 3–4 using 10% HCT and the white precipitate was filtered and then separated. Then, 29.2 g of the white precipitate and 11.2 g of KOH were dissolved in 150 mL of distilled water and then added with 1.14 g of BTEAC. Methacryloyl chloride (12.54 g) was slowly added to the mixture at room temperature dropwise and then allowed to react for 5 hr. Upon separation from the organic phase, the mixture was washed with distilled water several times and MC was evaporated under a reduced pressure to obtain a light yellow monomer having $_nD^{20.1}$:1.6059. The yield was 78%.

$^1$H-NMR (DMSO-d$_6$): 1.44–1.62(m, 6H, CH$_2$), 1.98(s, 6H, CH$_3$), 3.63–3.74(m, 4H, CH$_2$), 6.62(m, 2H, CH$_2$), 6.81(m, 2H, CH$_2$), 6.99(m, 4H, aromatic), 7.20(m, 4H), 7.43(m, 4H, aromatic), 7.57(m, 4H, aromatic)

EXAMPLE 7

Composition for Thermosetting

The monomer (39.6% by wt) obtained from the Example 2, 36.6% by wt of bis(4-acryloylbenzene)sulfide, 22.8% by wt of the compound in the preparation example 7 and 1.0% by wt of t-butylperoxybenzoate as an initiator were mixed together. The mixture was stirred for 30 min, defoamed and obtained a composition with $_nD^{24.9}$:1.610. The composition was then introduced into a mold by nitrogen pressure, placed under thermosetting of 1 hr at room temperature, 3 hr at 50° C., 5 hr at 80° C. and 5 hr at 100° C., and finally a transparent plastic sheet having $_nD^{25}$:1.6360 and 45.6 of Abbe number was obtained.

EXAMPLE 8

Composition for Thermosetting

The monomer (10.3% by wt) obtained from the Example 4, 70% by wt of the preparation example 7, 19.2% by wt of 2-mercaptoacetate(PTK$_2$) and 0.5% by wt of lauroyl peroxide as an initiator were mixed together and obtained a composition with $_nD^{24.9}$:1.588. The composition was then introduced into a mold by nitrogen pressure, placed under thermosetting of 1 hr at room temperature –45° C., 3 hr at 45° C., 2 hr at 45–65° C., 3 hr at 65° C., 2 hr. at 65–85° C., 2 hr at 85° C., 3 hr at 85–100° C., and 3 hr at 110° C., and finally a transparent plastic sheet having $_nD^{25}$:1.6205 and 36.3 of Abbe number was obtained.

EXAMPLE 9

Composition for Radiation Curing and Thermosetting

A composition was obtained by mixing 10.3% by wt of the monomer obtained from the example 2, 69% by wt of the preparation Example 7, 19.7% by wt of PTK$_2$ and 1.0% by wt of Irgacure 184 as an initiator. The composition was then introduced into a mold, irradiated by UV, and placed under thermosetting for 10 hr at 40–110° C., and finally a transparent plastic sheet having $_nD^{25}$:1.6126 and 37.6 of Abbe number was obtained.

EXAMPLES 10–14

Transparent plastic lenses were prepared according to the compositions and thermosetting conditions as shown in the following Table 1.

EXPERIMENTAL EXAMPLE

The functional analyses of the lenses prepared in the Examples 10–14 were performed by the following test methods.

[Test Methods]

(1) Thermal stability: Measured using TGA(Thermo Gravimetry Analysis) and DSC(Differential Scanning Calorimetry).

(2) Surface Hardness: Measured using a Pencil Scratching Tester (3) Light transparency: Measured at 400–800 nm via UV/Vis using 2 mm thick samples and the values at 600 nm were taken as mean values.

(4) Refractive Index: The refractive index of films were measured at room temperature using a prism coupler while molded products with more than 2 mm thickness were measured at 20° C. using "DR-A1" refractometer(ATAGO Co., Ltd., Japan).

(5) Water Adsorption: Samples were first immersed in water for 48 hr at room temperature and then water absorption was measured according to the change in weight after the immersion.

TABLE 1

| *Ex. | [1]T | wt % | [2]C | wt % | [3]O | wt % | [4]I | wt % | Curing Method | Refractive Index ($_nD^{20}$) | [5]PH | [6]LT (%) |
|---|---|---|---|---|---|---|---|---|---|---|---|---|
| 10 | Ex. 4 | 38 | **SF13 **SF18 | 20 20 | MS* | 10 | AIBN | 2 | TS[4] | 1.623 | >5 H | 93 |
| 11 | Ex. 5 | 30 | **SF14 | 20 | | | AIBN | 1 | TS & RC[6] | 1.651 | >6 H | 92 |
| | Ex. 7 | 20 | **SF17 | 28 | | | I184[3] | 1 | | | | |
| 12 | Ex. 4 | 50 | **SF18 | 25 | PKT$_2$[1] THF | 18 5 | I184[3] | 2 | RC[5] | 1.653 | >5 H | 89 |
| 13 | Ex. 4 | 50 | **SF18 | 20 | PKT$_3$[2] | 28 | I184[3] | 2 | TS & RC[6] | 1.671 | >5 H | 92 |
| 14 | Ex. 6 | 40 | **SF15 **SF17 **SF18 | 5 10 10 | MS* | 23 | BPO | 2 | TS[4] | 1.652 | >5 H | 93 |

[1]T: Triazine Type monomer
[2]C: Comonomer
[3]O: Other additives
[4]I: Initiator
[5]PH: Pencil Hardness
[6]LT: Light transparency
PKT$_2$[1]: pentaerythritoltetrakis(2-mercaptoacetate)
PKT$_3$[2]: pentaerythritoltetrakis(3-mercaptopropionate)
I184[3]: photo initiator (Ciba-Geigy Co., Ltd.)

TABLE 1-continued

| | Resin Composition | | | | | Refrac-tive | | |
|---|---|---|---|---|---|---|---|---|
| *Ex. [1)]T | wt % | [2)]C | wt % | [3)]O | wt % | [4)]I | wt % Curing Method | Index $(n_D^{20})$ | [5)]PH | [6)]LT (%) |

TS[4)]: thermosetting
RC[5)]: Radiation Curing
TS & RC[6)]: Thermosetting after Radiation Curing
*Ex. = Example
MS*: α-methylstyrene
-Water adsorption of the product in Examples 10–14 was lower than 1 wt % in all cases.

Triazine type monomers according to the present invention have refractive index of >1.60, and when cured as described in the Table 1, the triazine type monomers exhibit physical properties having refractive index of >1.65, Abbe number>35, water adsorption lower than 1%, and surface hardness>5H. In addition, thermal stability is >150° C. and transparency and abrasion resistance are shown to be excellent.

As described above, the triazine monomers manufactured according to the present invention are characterized by having high refractive index, improved workability and excellent compatibility with other unsaturated monomers and it thus enables to constitute a composition for thermosetting and radiation curing along with an initiator and a comonomer that can be polymerized. Thus manufactured products have high refractive index and Abbe number, excellent transparency, abrasion resistance and thermal stability and therefore can be used in optical products such as functional optical lenses, filters, imaging, display elements or optical integrated elements, holograms, optical discs, optical recording materials, optical pickup parts and the like.

What is claimed is:

1. A 1,3,5-triazine type monomer characterized by having at least one amine group and at least two sulfur atoms as expressed in the following formula (I),

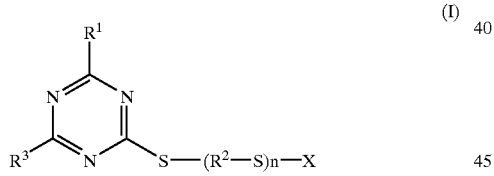

(I)

wherein $R^1$ is a secondary or a tertiary amine group selected from the group consisting of $R^4NH-$, $R^4R^5N-$ or

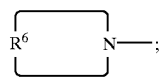

$R^4$ and $R^5$ are independently $C_1-C_{22}$ alkyl or cycloalkyl; $R^6$ is $C_1-C_{15}$ alkylene or an aromatic ring forming alkenes such as $-CH=CH-CH=CH-$ or $-CH=CH-CH_2-CH=CH-$; $R^2$ is $C_1-C_{22}$ linear alkylene, branched alkylene, or a 1,3-,1,4-benzene ring; $R^3$ is $R^1$ or $-S-(R^2-S)_n-X$; X is an acryl-, methacryl or $C_2-C_{10}$ alkene group; and n is an integer of 1–10.

2. A method of preparing 1,3,5-triazine type monomer according to claim 1, wherein said method comprises the following steps of:

(a) preparing triazine expressed in the following formula IV by reacting 2,4,6-trichloro-1,3,5-triazine with secondary- or tertiary amine;

(b) preparing triazine expressed in the following formula V by reacting said triazine obtained in the above step (a) with NaSH;

(c) preparing triazine expressed in the following formula VI by reacting said triazine obtained in the above step (b) with a thiol derivative expressed as $Y-(R^2-S)_n-H$ in the presence of a mixed catalyst; and (d) preparing triazine expressed in the above formula I by reacting said triazine obtained in the above step (c) with;
 (i) a compound selected from a group consisting of acryloyl chloride, methacryloyl chloride, and allyl bromide in the presence of a mixed catalyst; or
 (ii) propionyl chloride and then treat with a base,

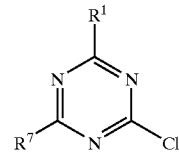

(IV)

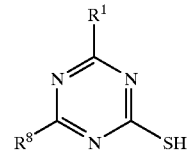

(V)

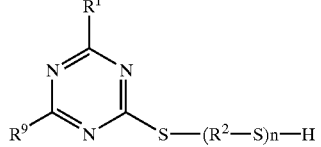

(VI)

wherein $R^1$ is a secondary or a tertiary amine group selected from a group consisting of $R^4NH-$, $R^4R^5N-$ or

$R^4$ and $R^5$ are independently $C_1-C_{22}$ alkyl or cycloalkyl; $R^6$ is $C_1-C_{15}$ alkylene or an aromatic ring forming alkenes such as $-CH=CH-CH=CH-$ or $-CH=CH-CH_2-CH=CH-$; $R^7$ is the same as $R^1$ or Cl; $R^8$ is the same as $R^1$ or SH; $R^9$ is the same as $R^1$ or $S-(R^2-S)_n-H$; $R^2$ is $C_1-C_{22}$ linear alkylene, branched alkylene, or a 1,3-,1,4-benzene ring; $R^3$ is $R^1$ or $-S-(R^2-S)_n-X$; X is an acryl-, methacryl or $C_2-C_{10}$ alkene group; n is an integer of 1–10; and Y is a leaving group selected from as Cl, Br or OH.

3. A polymerizable resin composition comprising 1–98 wt % of a monomer expressed in formula (I); 1–98 wt % of either an aromatic radical polymerizable monomer or a comonomer with an unsaturated group; and 0.5–5 wt % of an initiator wherein formula (I) is expressed as follows,

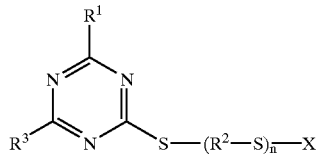
(I)

wherein $R^1$ is a secondary or a tertiary amine group selected from the group consisting of $R^4NH-$, $R^4R^5N-$ or

$R^4$ and $R^5$ are independently $C_1-C_{22}$ alkyl or cycloalkyl;

$R^6$ is $C_1-C_{15}$ alkylene or an aromatic ring forming alkenes such as $-CH=CH-CH=CH-$ or $-CH=CH-CH_2-CH=CH-$;

$R^2$ is $C_1-C_{22}$ linear alkylene, branched alkylene, or a 1,3-, 1,4-benzene ring;

$R^3$ is $R^1$ or $-S-(R^2-S)_n-X$; X is an acryl-, methacryl or $C_2-C_{10}$ alkene group; and n is an integer of 1–10.

4. A transparent optical product manufactured by using the monomer expressed in the above formula (I) or the resin composition in claim 3.

5. A method of manufacturing a plastic product by thermosetting of the resin composition in claim 3 at 10–130° C.

6. A method of manufacturing a plastic product by radiation curing of the resin composition in claim 3 at 10–130° C.

7. A method of manufacturing a plastic product by first radiation curing the resin composition in claim 3 at 10–130° C. followed by the thermosetting of the resin composition in claim 3 at 10–130° C.

* * * * *